US012103980B2

(12) United States Patent
Chen et al.

(10) Patent No.: US 12,103,980 B2
(45) Date of Patent: Oct. 1, 2024

(54) DEVELOPMENT OF RECOMBINANT CHICKEN IGY SCFV ANTIBODY RAISED AGAINST HUMAN THYMIDINE KINASE 1 EXPRESSED IN PROKARYOTIC CELLS AND USE THEREOF

(71) Applicant: SINO-SWED TONGKANG BIO-TECH (SHENZHEN) LIMITED, Guangdong (CN)

(72) Inventors: Hu Chen, Guangdong (CN); Zuosheng Li, Guangdong (CN); Huijun Li, Guangdong (CN); Liwen Liang, Guangdong (CN); Li Dang, Guangdong (CN); Senbo Liu, Guangdong (CN); Cong Fang, Guangdong (CN); Peng Gao, Guangdong (CN); Ellen He, Guangdong (CN); Sven Isac Skog, Guangdong (CN); Ji Zhou, Guangdong (CN)

(73) Assignee: SINO-SWED TONGKANG BIO-TECH (SHENZHEN) LIMITED, Shenzhen (CN)

( * ) Notice: Subject to any disclaimer, the term of this patent is extended or adjusted under 35 U.S.C. 154(b) by 882 days.

(21) Appl. No.: 17/191,722

(22) Filed: Mar. 4, 2021

(65) Prior Publication Data
US 2021/0189010 A1      Jun. 24, 2021

Related U.S. Application Data

(63) Continuation of application No. PCT/CN2019/102620, filed on Aug. 26, 2019.

(30) Foreign Application Priority Data

Sep. 5, 2018   (CN) .......................... 201811029929.1

(51) Int. Cl.
*C07K 16/40*        (2006.01)
*A61K 47/68*        (2017.01)

(52) U.S. Cl.
CPC .......... *C07K 16/40* (2013.01); *A61K 47/6871* (2017.08); *C07K 2317/14* (2013.01); *C07K 2317/622* (2013.01); *C12Y 207/01021* (2013.01); *G01N 2333/9122* (2013.01)

(58) Field of Classification Search
None
See application file for complete search history.

(56) References Cited

U.S. PATENT DOCUMENTS

| 2004/0141980 A1* | 7/2004 | Ignjatovic ............... A61P 31/14 530/388.3 |
|---|---|---|
| 2010/0036091 A1 | 2/2010 | Robinson et al. |
| 2016/0311927 A1 | 10/2016 | Eriksson |
| 2018/0105600 A1 | 4/2018 | Pons et al. |

FOREIGN PATENT DOCUMENTS

| CN | 101027085 A | | 8/2007 |
|---|---|---|---|
| CN | 102432683 A | | 5/2012 |
| CN | 102504027 A | | 6/2012 |
| CN | 102516390 A | | 6/2012 |
| CN | 103483449 A | | 1/2014 |
| CN | 105384815 A | * | 3/2016 |
| CN | 105980407 A | | 9/2016 |
| CN | 106554950 A | | 4/2017 |
| CN | 106556592 A | | 4/2017 |
| CN | 107365753 A | | 11/2017 |
| WO | 2018145533 A1 | | 8/2018 |

OTHER PUBLICATIONS

F. Zhang, X. Shao, H. Li, J.G. Robison, B.K. Murray, and K.L. O'Neill, "A Monoclonal Antibody Specific for Human Thymidine Kinase 1", HYBRIDOMA, vol. 20, No. 1, 2001, pp. 25-34.
Chuanjing Wu, Rong Jiang Yang, Ji Zhou, Shing Bao, Li Zou, Pinggan Zhang, Yongrong Mao, Jianping Wu, Qimin He, "Production and characterisation of a novel chicken IgY antibody raised against C-terminal peptide from human thymidine kinase 1", Journal of Immunological Methods, 277 (2003), 157-169.
Ding Ke-Xiang , Zheng Yong-Chen , Wu Zhao-Yang, et al., "Preparing monoclone antibody of human thymidine kinase", Chinese Journal of Gerontology, Jan. 2005, vol. 25, pp. 54-55, China Academic Journal Electronic Publishing House.
International Search Report in corresponding PCT Application No. PCT/CN2019/102620, dated Nov. 27, 2019; and Written Opinion of the International Searching Authority in corresponding PCT Application No. PCT/CN2019/102620, dated Nov. 27, 2019.
First Office Action in counterpart China Application No. 201811029929.1, dated Mar. 17, 2022.
Notification to Grant Patent Right for Invention in counterpart China Application No. 201811029929.1, dated Jul. 15, 2022.
Sapats, S. I. et al., GenBank, Accession No. AAR01543.1, "immunoglobulin G scFv antibody CRAb19, partial [synthetic construct]", Jul. 26, 2016.
Sapats, S. I. et al., GenBank, Accession No. AAO15855.1, "immunoglobulin G single chain variable fragment, partial [synthetic construct]", Jul. 24, 2016.
Q. He et al., "The clinical significance of thymidine kinase 1 measurement in serum of breast cancer patients using anti-TK1 antibody", The International Journal of Biological Markers, 2000, vol. 15, No. 2, pp. 139-146.
Jayson V. Pagaduan et al., "Microchip Immunoaffinity Electrophoresis of Antibody-Thymidine Kinase 1 Complex", Electrophoresis, 2015, vol. 36, No. 5, pp. 813-817, DOI: 10.1002/elps.201400436.

(Continued)

*Primary Examiner* — Daniel E Kolker
*Assistant Examiner* — Maureen Varina Driscoll (57) ABSTRACT

Disclosed are the expression of a recombinant chicken IgY scFv antibody and monoclonal antibody raised against human thymidine kinase 1 (hTK1) in prokaryotic cells and a preparation method and use thereof. The scFv antibody includes an amino acid sequence shown in SEQ ID NO: 1. The anti-hTK1 recombinant scFv antibody and monoclonal antibody have good immunoreactivity, high specificity and sensitivity, and are easy to separate and purify.

12 Claims, 3 Drawing Sheets

Specification includes a Sequence Listing.

(56) References Cited

OTHER PUBLICATIONS

Boles, K. S. et al., GenBank, Accession No. KY199429.1, "Synthetic construct lucentis heavy chain and lucentis light chain genes, complete cds", Jul. 18, 2017.
Van Wyngaardt, W. et al., GenBank, Accession No. AAR11513.1, "immunoglobulin single chain variable fragment Hca12 [synthetic construct]", May 13, 2004.
Kiran Kumar Jagarlamudi et al., "Thymidine kinase 1 as a tumor biomarker: technical advances offer new potential to an old biomarker", Biomarkers in Medicine, 2018, vol. 12, No. 9, pp. 1035-1048.
Kiran Kumar Jagarlamudi et al., "Breast and prostate cancer patients differ significantly in their serum Thymidine kinase 1 (TK1) specific activities compared with those hematological malignancies and blood donors: implications of using serum TK1 as a biomarker", BMC Cancer, 2015, 15:66, pp. 1-12, DOI: 10.1186/s12885-015-1073-8.

* cited by examiner

SEQUENCE LISTING

```
<160> NUMBER OF SEQ ID NOS: 4

<210> SEQ ID NO 1
<211> LENGTH: 249
<212> TYPE: PRT
<213> ORGANISM: Artificial
<220> FEATURE:
<223> OTHER INFORMATION: Antibody

<400> SEQUENCE: 1

Ala Val Thr Leu Asp Glu Ser Gly Gly Gly Leu Gln Thr Pro Gly Gly
1               5                   10                  15

Thr Leu Ser Leu Val Cys Lys Ala Ser Gly Phe Thr Phe Ser Asp Tyr
            20                  25                  30

Gly Met Asn Trp Val Arg Gln Ala Pro Gly Lys Gly Leu Glu Phe Val
        35                  40                  45

Ala Gly Ile Glu Asn Asp Gly Ser Ser Thr Trp Tyr Ala Thr Ala Val
    50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Ala Thr Tyr Phe Cys
```

```
                85                  90                  95
Ala Lys Asp Phe Ser Ser Gly Tyr Gly Gly Trp Ser Ala Ser Gly Gly
                    100                 105                 110

Ile Asp Ala Trp Gly His Gly Thr Glu Val Ile Val Ser Ser Gly Gly
            115                 120                 125

Gly Ser Gly Gly Gly Ser Gly Gly Gly Ser Gly Gly Gly Ser
        130                 135                 140

Ala Leu Thr Gln Pro Ser Ser Val Ser Ala Asn Pro Gly Glu Thr Val
145                 150                 155                 160

Lys Ile Thr Cys Ser Gly Asp Arg Ser Ser Tyr Tyr Gly Tyr Tyr Gly
                165                 170                 175

Trp Tyr Gln Gln Lys Ala Pro Gly Ser Ala Pro Leu Thr Val Ile Tyr
            180                 185                 190

Tyr Ser Ser Asn Arg Pro Thr Asn Ile Pro Ser Arg Phe Ser Gly Ser
                195                 200                 205

Lys Ser Gly Ser Thr Ala Thr Leu Thr Ile Thr Gly Val Arg Ala Glu
        210                 215                 220

Asp Glu Ala Val Tyr Tyr Cys Gly Ser Ala Glu Asp Ser Ser Tyr Ala
225                 230                 235                 240

Ala Ile Phe Gly Ala Gly Thr Thr Leu
                245
```

<210> SEQ ID NO 2
<211> LENGTH: 896
<212> TYPE: DNA
<213> ORGANISM: Artificial
<220> FEATURE:
<223> OTHER INFORMATION: Nucleic Acid

<400> SEQUENCE: 2

```
atccatggat gctgttaccc tggacgaatc tggtggtggt ctgcagaccc cgggtggtac     60
cctgtctctg gtttgcaaag cttctggttt caccttctct gactacggta tgaactgggt    120
tcgtcaggct ccgggtaaag gtctggaatt cgttgctggt atcgaaaacg acggttcttc    180
tacctggtac gctaccgctg ttaaaggtcg tgctaccatc tctcgtgaca acggtcagtc    240
taccgttcgt ctgcagctga caaacctgcg tgctgaagac accgctacct acttctgcgc    300
taaagacttc tcttctggtt acggtggttg gtctgcttct ggtggtatcg acgcttgggg    360
tcacggtacc gaagttatcg tttcttctgg tggtggttct ggtggtggtg ttctggtgg    420
tggtggttct ggtggtggtt ctgctctgac ccagccgtct tctgtttctg ctaacccggg    480
tgaaaccgtt aaaatcacct gctctggtga ccgttcttct tactacggtt actacggttg    540
gtaccagcag aaagctccgg ttctgctccg ctgaccgtt atctactact cttctaaccg    600
tccgaccaac atcccgtctc gtttctctgg ttctaaatct ggttctaccg ctaccctgac    660
catcaccggt gttcgtgctg aagacgaagc tgtttactac tgcggttctg ctgaagactc    720
ttcttacgct gctatcttcg gtgctggtac caccctggct gctgctgctg ctatggacga    780
aaaaaccacc ggttggcgtg tggtcacgt tgttgaaggt ctggctggtg aactggaaca    840
gctgcgtgct cgtctggaac caccccgca gggtcagcgt gaaccggcgg ccgcat        896
```

<210> SEQ ID NO 3
<211> LENGTH: 747
<212> TYPE: DNA
<213> ORGANISM: Artificial
<220> FEATURE:
<223> OTHER INFORMATION: Antibody

```
<400> SEQUENCE: 3
gcagtgacgt tggacgagtc cgggggcggc ctccagacgc ccggaggaac gctcagcctc      60
gtctgcaagg cctccgggtt caccttcagc gattatggca tgaactgggt gcgacaggcg     120
cccggcaagg ggctggagtt cgtcgctggt attgagaatg atggtagtag cacatggtac     180
gcgacggcgg tgaagggccg tgccaccatc tcgagggaca acgggcagag cacagtgagg     240
ctgcagctga acaacctcag ggctgaggac accgccacct acttctgcgc caaagatttt     300
agtagtggtt atggtggttg gagtgcttct ggtggcatcg acgcatgggg ccacgggacc     360
gaagtcatcg tctcctctgg tggaggatca ggtggaggag gatccggagg tggtggttct     420
ggaggtggtt ctgcgctgac tcagccgtcc tcggtgtcag caaacccggg agaaaccgtc     480
aagatcacct gctccgggga tcggagcagc tactatggtt actatggctg gtatcagcag     540
aaggcacctg gcagtgcccc tctcactgtg atctattaca gcagcaacag acccacgaac     600
atcccttcac gattctctgg ttccaaatcc ggctccacag ccacattaac catcactggg     660
gtccgagccg aggacgaggc tgtctattac tgtgggagtg cagaagacag cagctatgct     720
gctatatttg gggccgggac aaccctg                                         747

<210> SEQ ID NO 4
<211> LENGTH: 114
<212> TYPE: DNA
<213> ORGANISM: Artificial
<220> FEATURE:
<223> OTHER INFORMATION: SBP-tag

<400> SEQUENCE: 4
atggacgaaa aaaccaccgg ttggcgtggt ggtcacgttg ttgaaggtct ggctggtgaa      60
ctggaacagc tgcgtgctcg tctggaacac cacccgcagg gtcagcgtga accg           114
```

DEVELOPMENT OF RECOMBINANT CHICKEN IGY SCFV ANTIBODY RAISED AGAINST HUMAN THYMIDINE KINASE 1 EXPRESSED IN PROKARYOTIC CELLS AND USE THEREOF

CROSS-REFERENCE TO RELATED APPLICATIONS

This application is a Continuation Application of International Application No. PCT/CN2019/102620, filed on Aug. 26, 2019, which claims priority to Chinese Application No. 201811029929.1, filed on Sep. 5, 2018, the entire disclosure of which is incorporated herein by reference.

This application contains a sequence listing submitted as an ASCII text file, named "Seq-List.txt" and created on Mar. 4, 2021, with 5,098 bytes in size. The material in the above-identified ASCII text file is incorporated herein by reference in its entirety.

TECHNICAL FIELD

The present disclosure relates to the field of bioengineering, specifically to a single-chain antibody or a monoclonal antibody raised against human thymidine kinase 1 expressed in prokaryotic cell, and a preparation method and use thereof, more specifically to a single-chain antibody or a monoclonal antibody, an isolated RNA, a suitable vector, an expression in prokaryotic cell, a method for preparing a single-chain antibody or a monoclonal antibody, an immunoconjugate, a test strip or a test kit, and a use of a single-chain antibody or a monoclonal antibody, an immunoconjugate and a test strip or a test kit to detect abnormal cell proliferation.

BACKGROUND

Human Thymidine Kinase 1 (hTK1) is a key enzyme during the DNA synthesis process of human cell proliferation, and is related to the rate of abnormal cell proliferation. It was coformed that hTK1 activity is minimal or undetectable in human serum from healthy people, but elevated in patients with malignant tumors, accompanied by rapid proliferation of tumor cells. At present, the non-invasive serological marker of serum TK1 assay is not only useful in the clinical evaluation of prognosis, recurrence risk and survival effect of cancer patients but also useful for early tumor screening in health examination for the risk of developing tumors based on data of 160,086 people who underwent health examination at four independent routine health screening centers in China from 2005 to 2018.

The protein monomer molecule of hTK1 is composed of 234 amino acids, and the active form is a tetramer composed of 4 monomers. Nowadays, compression with chicken-derived anti-hTK1 IgY-polyclonal antibodies (HTK1-IgY-pAb), most mouse-derived anti-hTK1 monoclonal antibodies have good stability, but lack specificity. It is also due to the selection of key epitopes in the primary sequence of hTK1 protein and the technical skills of purification, the murine-derived anti-hTK1 monoclonal antibodies have low sensitivity and limited to many hTK1 detection in the population. However, there is a difference in the stability of the antibody due to the prepared antibodies by difference of hen, it also limited the application of many health screening. Therefore, it is necessary to study a chicken-derived recombinant IgY monoclonal antibody against htk1 with high specificity, high sensitivity and good stability for large-scale health screening.

SUMMARY

The present disclosure aims to solve at least one of the technical problems existing in the related art. To this end, an object of the present disclosure is to provide a recombinant single-chain antibody or monoclonal antibody. The single-chain antibody or monoclonal antibody is an anti-hTK1 IgY single-chain or monoclonal antibody. Those antibodies have good immunoreactivity, high specificity and sensitivity, and are easy to separate and purify.

It should be noted that the present disclosure is completed based on the following work of the inventors.

The inventors obtained a nucleotide sequence shown in SEQ ID NO: 2 after codon optimization of a chicken-derived anti-hTK1 recombinant single-chain antibody gene sequence (including a sequence shown in SEQ ID NO: 3) obtained from the previous research and after the addition of SBP-tag. By constructing a recombinant pET22b expression vector, expressing soluble single-chain antibody protein in the periplasmic space of BL21(DE3) cells, and extracting and purifying by affinity chromatography on agarose gel column coupled with an antigen (C-terminal 31-peptide of hTK1), the anti-hTK1 single-chain recombinant antibody with high purity, high activity, and high specificity was obtained. The sequence shown in SEQ ID NO: 3 is as follows:

(SEQ ID NO: 3)
GCAGTGACGTTGGACGAGTCCGGGGGCGGCCTCCAGACGCCCGGAGGA

ACGCTCAGCCTCGTCTGCAAGGCCTCCGGGTTCACCTTCAGCGATTATGG

CATGAACTGGGTGCGACAGGCGCCCGGCAAGGGGCTGGAGTTCGTCGCTG

GTATTGAGAATGATGGTAGTAGCACATGGTACGCGACGGCGGTGAAGGGC

CGTGCCACCATCTCGAGGGACAACGGGCAGAGCACAGTGAGGCTGCAGCT

GAACAACCTCAGGGCTGAGGACACCGCCACCTACTTCTGCGCCAAAGATT

TTAGTAGTGGTTATGGTGGTTGGAGTGCTTCTGGTGGCATCGACGCATGG

GGCCACGGGACCGAAGTCATCGTCTCCTCTGGTGGAGGATCAGGTGGAGG

AGGATCCGGAGGTGGTGGTTCTGGAGGTGGTTCTGCGCTGACTCAGCCGT

CCTCGGTGTCAGCAAACCCGGGAGAAACCGTCAAGATCACCTGCTCCGGG

GATCGGAGCAGCTACTATGGTTACTATGGCTGGTATCAGCAGAAGGCACC

TGGCAGTGCCCCTCTCACTGTGATCTATTACAGCAGCAACAGACCCACGA

ACATCCCTTCACGATTCTCTGGTTCCAAATCCGGCTCCACAGCCACATTA

ACCATCACTGGGGTCCGAGCCGAGGACGAGGCTGTCTATTACTGTGGGAG

TGCAGAAGACAGCAGCTATGCTGCTATATTTGGGGCCGGGACAACCCTG

Therefore, according to a first aspect of the present disclosure, the present disclosure provides a single-chain antibody. According to an embodiment of the present disclosure, the single-chain antibody includes an amino acid sequence shown in SEQ ID NO: 1, the amino acid sequence shown in SEQ ID NO:1 is as follows:

(SEQ ID NO: 1)
AVTLDESGGGLQTPGGTLSLVCKASGFTFSDYGMNWVRQAPGKGLEFVAG

IENDGSSTWYATAVKGRATISRDNGQSTVRLQLNNLRAEDTATYFCAKDF

SSGYGGWSASGGIDAWGHGTEVIVSSGGGSGGGGSGGGGSGGGSALTQPS

SVSANPGETVKITCSGDRSSYYGYYGWYQQKAPGSAPLTVIYYSSNRPTN

IPSRFSGSKSGSTATLTITGVRAEDEAVYYCGSAEDSSYAAIFGAGTTL

The inventors surprisingly found that the anti-hTK1 recombinant single-chain antibody has good immunoreactivity, high specificity and sensitivity, and is easy to separate and purify.

According to a second aspect of the present disclosure, the present disclosure provides a monoclonal antibody. According to an embodiment of the present disclosure, the monoclonal antibody includes the amino acid sequence shown in SEQ ID NO: 1. the inventors surprisingly found that the anti-hTK1 recombinant monoclonal antibody has good immunoreactivity, high specificity and sensitivity, and is easy to separate and purify.

According to a third aspect of the present disclosure, the present disclosure provides an isolated nucleic acid. The nucleic acid encodes the single-chain antibody or the monoclonal antibody. The single-chain antibody or monoclonal antibody encoded by the nucleic acid according to an embodiment of the present disclosure has the advantages of good immunoreactivity, high specificity and sensitivity, and easy separation and purification.

According to an embodiment of the present disclosure, the nucleic acid includes a nucleotide sequence shown in SEQ ID NO: 2, the nucleotide sequence shown in SEQ ID NO: 2 is as follows:

(SEQ ID NO: 2)
ATCCATGGATGCTGTTACCCTGGACGAATCTGGTGGTGGTCTGCAGACCC

CGGGTGGTACCCTGTCTCTGGTTTGCAAAGCTTCTGGTTTCACCTTCTCT

GACTACGGTATGAACTGGGTTCGTCAGGCTCCGGGTAAAGGTCTGGAATT

CGTTGCTGGTATCGAAAACGACGGTTCTTCTACCTGGTACGCTACCGCTG

TTAAAGGTCGTGCTACCATCTCTCGTGACAACGGTCAGTCTACCGTTCGT

CTGCAGCTGAACAACCTGCGTGCTGAAGACACCGCTACCTACTTCTGCGC

TAAAGACTTCTCTTCTGGTTACGGTGGTTGGTCTGCTTCTGGTGGTATCG

ACGCTTGGGGTCACGGTACCGAAGTTATCGTTTCTTCTGGTGGTGGTTCT

GGTGGTGGTGGTTCTGGTGGTGGTGGTTCTGGTGGTGGTTCTGCTCTGAC

CCAGCCGTCTTCTGTTTCTGCTAACCCGGGTGAAACCGTTAAAATCACCT

GCTCTGGTGACCGTTCTTCTTACTACGGTTACTACGGTTGGTACCAGCAG

AAAGCTCCGGGTTCTGCTCCGCTGACCGTTATCTACTACTCTTCTAACCG

TCCGACCAACATCCCGTCTCGTTTCTCTGGTTCTAAATCTGGTTCTACCG

CTACCCTGACCATCACCGGTGTTCGTGCTGAAGACGAAGCTGTTTACTAC

TGCGGTTCTGCTGAAGACTCTTCTTACGCTGCTATCTTCGGTGCTGGTAC

CACCCTGGCTGCTGCTGCTGCTATGGACGAAAAAACCACCGGTTGGCGTG

GTGGTCACGTTGTTGAAGGTCTGGCTGGTGAACTGGAACAGCTGCGTGCT

CGTCTGGAACACCACCCGCAGGGTCAGCGTGAACCGGCGGCCGCAT

According to a fourth aspect of the present disclosure, the present disclosure provides a vector. According to an embodiment of the present disclosure, the vector includes the nucleic acid. After the vector according to the embodiment of the present disclosure is introduced into recipient cells, it can secrete and produce anti-hTK1 single-chain antibody or monoclonal antibody. The single-chain antibody or monoclonal antibody has good immunoreactivity, high specificity and sensitivity, and is easy to separate and purify.

According to an embodiment of the present disclosure, the vector is a prokaryotic expression vector. Therefore, it is convenient to transform the vector into prokaryotic cells and prepare the anti-hTK1 recombinant single-chain antibody or monoclonal antibody in the prokaryotic cells.

According to a fifth aspect of the present disclosure, the present disclosure provides a recombinant cell. According to an embodiment of the present disclosure, the recombinant cell includes the aforementioned vector. The recombinant cell according to the embodiment of the present disclosure can secrete and produce anti-hTK1 recombinant single-chain antibody or monoclonal antibody. The single-chain antibody or monoclonal antibody has good immunoreactivity, high specificity and sensitivity, and is easy to separate and purify.

According to a sixth aspect of the present disclosure, the present disclosure provides a method for preparing the aforementioned single-chain antibody or monoclonal antibody. According to an embodiment of the present disclosure, the method includes: culturing the aforementioned recombinant cell under conditions suitable for protein expression and secretion, so as to obtain the single-chain antibody or monoclonal antibody. Therefore, the single-chain antibody or monoclonal antibody prepared by the method has good immunoreactivity, high specificity and sensitivity, and is easy to separate and purify. The method has the advantages of high expression, easy expansion and reproduction, and low cost.

According to a seventh aspect of the present disclosure, the present disclosure provides an immunoconjugate. According to an embodiment of the present disclosure, the immunoconjugate includes the aforementioned single-chain antibody or monoclonal antibody, and a conjugate moiety selected from the group consisting of drugs, toxins, cytokines, radionuclides or enzymes. The immunoconjugate according to the embodiment of the present disclosure can effectively improve the drug effect of the conjugate moiety by coupling with the single-chain antibody or monoclonal antibody, and has a better curative effect on abnormal cell diseases, such as tissue hyperplasia and tumor.

According to an eighth aspect of the present disclosure, the present disclosure provides a test strip or test kit. According to an embodiment of the present disclosure, the test strip and the test kit include the aforementioned single-chain antibody or monoclonal antibody, the aforementioned immunoconjugate, or their combination with a detectable marker. Therefore, the test strip or test kit can be used to detect TK1, and then determine the abnormal proliferation of cells. In addition, the detection strip or the detection kit has high detection sensitivity and good specificity.

According to a ninth aspect of the present disclosure, the present disclosure provides a use of the aforementioned single-chain antibody or monoclonal antibody, the aforementioned immunoconjugate, and the aforementioned test strip or test kit for detecting abnormal cell proliferation. Therefore, the aforementioned single-chain antibody or monoclonal antibody, the aforementioned immunoconjugate, and the aforementioned test strip or test kit can be used to detect TK1 to determine abnormal cell proliferation, with high detection sensitivity and good specificity.

According to an embodiment of the present disclosure, the abnormal cell proliferation includes pregnancy, tissue hyperplasia and tumor.

The additional aspects and advantages of the present disclosure will be partly given in the following description, and part will become obvious from the following description, or be understood through the practice of the present disclosure.

BRIEF DESCRIPTION OF THE DRAWINGS

The above and/or additional aspects and advantages of the present disclosure will become obvious and easy to understand from the description of the embodiments in combination with the following drawings.

DETAILED DESCRIPTION OF THE EMBODIMENTS

The embodiments of the present disclosure are described in detail below, and examples of the embodiments are shown in the accompanying drawings. The same or similar reference numerals indicate the same or similar elements or elements with the same or similar functions. The embodiments described below with reference to the drawings are exemplary, and are only used to explain the present disclosure, but should not be understood as limiting the present disclosure.

After long-term and in-depth research, the inventors modified the gene encoding anti-hTK1 single-chain antibody or monoclonal antibody. Based on this, a prokaryotic expression system that specifically expresses anti-hTK1 recombinant single-chain antibody or monoclonal antibody was constructed, and the anti-hTK1 recombinant single-chain antibody or monoclonal antibody produced by the expression system was used to detect TK1, thereby determining the abnormal proliferation of cells, which was used as one of the indicators to determine pregnancy, tissue proliferation and tumor. On this basis, the inventor completed the present disclosure.

Specifically, it is known in the art that prokaryotic expression systems have the disadvantages of difficulty in purification of the target protein, incomplete post-translational processing and modification systems of prokaryotic expression systems, and low biological activity of expression products. Therefore, the eukaryotic expression system is often used in the preparation of TK1 antibody in the art. However, the preparation process using eukaryotic expression system is cumbersome, it is extremely difficult to screen out specific antibodies, and the cost is also high.

The inventors of the present disclosure unexpectedly discovered through research that by constructing a prokaryotic expression system for anti-hTK1 recombinant single-chain antibody or monoclonal antibody, not only can the anti-hTK1 recombinant single-chain antibody or monoclonal antibody be easily purified, but also the affinity, specificity and sensitivity of the anti-hTK1 recombinant single-chain antibody or monoclonal antibody are highly sensitive immune response with hTK1. The recombinant single-chain antibody or monoclonal antibody specifically targets hTK1 and can be used for early detection of abnormal clinical cell proliferation.

Single-chain antibody, monoclonal antibody and expression and preparation thereof.

According to a first aspect of the present disclosure, the present disclosure provides a single-chain antibody. According to an embodiment of the present disclosure, the single-chain antibody includes an amino acid sequence shown in SEQ ID NO: 1. the inventors surprisingly found that the anti-hTK1 single-chain antibody has good immunoreactivity, high specificity and sensitivity, and is easy to separate and purify.

The term "single-chain antibody" as used herein is an antibody formed by linking the variable region of the heavy chain of the antibody and the variable region of the light chain of the antibody through a short peptide (linker). Specifically, single-chain antibodies do not have a constant region, but the functions and immune effects of single-chain antibodies and monoclonal antibodies in the examples of the present disclosure are the same and similar.

According to a second aspect of the present disclosure, the present disclosure provides a monoclonal antibody. According to an embodiment of the present disclosure, the monoclonal antibody includes the amino acid sequence shown in SEQ ID NO: 1. the inventors surprisingly found that the anti-hTK1 monoclonal antibody has good immunoreactivity, high specificity and sensitivity, and is easy to separate and purify.

The term "monoclonal antibody" as used herein refers to an antibody obtained from a population of substantially homologous antibodies, that is, the antibodies that make up the population are all the same, except that there may be a small number of possible spontaneous mutations. Therefore, the modifier "monoclonal" means that the nature of the antibody is not a mixture of discrete antibodies.

According to a third aspect of the present disclosure, the present disclosure provides an isolated nucleic acid. The nucleic acid encodes the aforementioned single-chain antibody or monoclonal antibody. The single-chain antibody or monoclonal antibody encoded by the nucleic acid according to the embodiment of the present disclosure has the advantages of good immunoreactivity, high specificity and sensitivity, and easy separation and purification.

The inventors added SBP-tag to the nucleotide sequence encoding the aforementioned single-chain antibody or monoclonal antibody and performed codon optimization. The sequence of SBP-tag is as follows:

(SEQ ID NO: 4)
ATGGACGAAAAAACCACCGGTTGGCGTGGTGGTCACGTTGTTGAAGGTC

TGGCTGGTGAACTGGAACAGCTGCGTGCTCGTCTGGAACACCACCCGCAG

GGTCAGCGTGAACCG

Based on the above optimization, according to an embodiment of the present disclosure, the nucleic acid includes the nucleotide sequence shown in SEQ ID NO: 2. the nucleotide sequence is the coding sequence of the aforementioned anti-hTK1 single-chain antibody or monoclonal antibody. This sequence is more suitable for translation and expression of antibody genes in *Escherichia coli* based on codon preference.

It should be noted that DNA is transcribed into mRNA, and mRNA is processed by splicing and other processes to translate into protein. The so-called coding sequence is the DNA sequence corresponding to the protein sequence one-to-one. The sequence does not contain other sequences that are not corresponding to the protein, and does not consider sequence changes during the process of mRNA processing, etc. In short, the coding sequence corresponds exactly to the codon of the protein. In other words, the coding sequence is the sequence that encodes a protein product.

In the present disclosure, the nucleic acid further includes a nucleotide sequence in which one or more bases are substituted, deleted, or modified to the nucleotide sequence SEQ ID NO: 2, referring to the substitution, deletion, and addition of no more than 2-45 bases, or no more than 2-30 bases, or no more than 3-20 bases, or no more than 4-15 bases, or no more than 5-10 bases, or no more than 6-8 bases represented by consecutive integers at the 5'-terminal and/or 3'-terminal of the nucleotide sequence separately or simultaneously and/or within the sequence.

In the present disclosure, the nucleic acid further includes a nucleotide sequence in which one or more bases are substituted, deleted, or modified to the nucleotide sequence SEQ ID NO: 2, which has the same or similar anti-hTK1 single-chain antibody or monoclonal antibody function with the nucleotide sequence SEQ ID NO: 1, SEQ ID NO: 2 or SEQ ID NO: 3.

According to a fourth aspect of the present disclosure, the present disclosure provides a vector. According to an embodiment of the present disclosure, the vector includes the aforementioned nucleic acid. After the vector according to the embodiment of the present disclosure is introduced into recipient cells, it can secrete and produce anti-hTK1 single-chain antibody or monoclonal antibody. The single-chain antibody or monoclonal antibody has good immunoreactivity, high specificity and sensitivity, and is easy to separate and purify.

According to an embodiment of the present disclosure, the vector is a prokaryotic expression vector, such as a pET expression vector, T-type. Therefore, it is convenient to transform the vector into prokaryotic cells and prepare anti-hTK1 monoclonal antibodies in prokaryotic cells.

The vector can be obtained by, for example, inserting the above-mentioned nucleotide sequence into a cloning vector or expression vector, or can be obtained by artificial synthesis. For example, construction of the recombinant antibody expression vector cab be sued in *E. coli* and a virus system.

According to a fifth aspect of the present disclosure, the present disclosure provides a host cell. According to an embodiment of the present disclosure, the host cell includes the aforementioned vector. The host cell according to the embodiment of the present disclosure can secrete and produce anti-hTK1 single-chain antibody or monoclonal antibody. The single-chain antibody or monoclonal antibody has good immunoreactivity, high specificity and sensitivity, and is easy to separate and purify.

According to some embodiments of the present disclosure, the recombinant antibody can be obtained by transforming the aforementioned vector into a host cell.

According to a sixth aspect of the present disclosure, the present disclosure provides a method for preparing the aforementioned single-chain antibody or monoclonal antibody. According to an embodiment of the present disclosure, the method includes: culturing the host cells encoding the scFv/monoclonal antibody under conditions suitable for TK1 protein expression and secretion, so as to obtain the single-chain antibody or monoclonal antibody. Therefore, the scFv/monoclonal antibody prepared by the method has good immunoreactivity, high specificity and sensitivity, and is easy to separate and purify.

According to some embodiments of the present disclosure, the method further includes purifying the single-chain antibody or monoclonal antibody. The purification treatment can be carried out by affinity chromatography on agarose gel column with TK1-31 amino acid coupling polypeptide antigen. Thus, the single-chain antibody or monoclonal antibody obtained by the purification treatment has high purity and activity.

Immunoconjugate, Test Strip or Test Kit and Use Thereof

According to a seventh aspect of the present disclosure, the present disclosure provides an immunoconjugate. According to an embodiment of the present disclosure, the immunoconjugate includes the aforementioned single-chain antibody or monoclonal antibody, and a conjugate moiety selected from the group consisting of drugs, toxins, cytokines, radionuclides or enzymes. The immunoconjugate according to the embodiment of the present disclosure can effectively improve the drug effect of the conjugate moiety by coupling with the single-chain antibody or monoclonal antibody, and has a better curative effect on abnormal cell diseases, such as tissue hyperplasia and tumor.

According to an eighth aspect of the present disclosure, the present disclosure provides a test strip or test kit. According to an embodiment of the present disclosure, the test strip and the test kit include the aforementioned single-chain antibody or monoclonal antibody, the aforementioned immunoconjugate, or their combination with a detectable marker. Therefore, the test strip or test kit can be used to detect TK1, and then determine the abnormal proliferation of cells. In addition, the detection strip or the detection kit has high detection sensitivity and good specificity.

According to a preferred embodiment of the present disclosure, the detectable marker is selected from: colloidal gold marker, fluorescent marker, isotope marker, enzyme marker, preferably the enzyme marker is HRP enzyme marker.

According to a ninth aspect of the present disclosure, the present disclosure provides a use of the aforementioned single-chain antibody or monoclonal antibody, the aforementioned immunoconjugate, and the aforementioned test strip or test kit for detecting abnormal cell proliferation. Therefore, the aforementioned single-chain antibody or monoclonal antibody, the aforementioned immunoconjugate, and the aforementioned test strip or test kit can be used to detect TK1 to determine abnormal cell proliferation, with high detection sensitivity and good specificity.

There are many cases of abnormal cell proliferation. For the anti-hTK1 single-chain antibody or monoclonal antibody of the embodiment of the present disclosure, the abnormal cell proliferation can include pregnancy, tissue hyperplasia and tumor, and the detection sensitivity and accuracy are high.

The present disclosure will be described below with reference to specific embodiments. It should be noted that these embodiments are merely illustrative and should not be understood as limiting the present disclosure.

The solution of the present disclosure will be explained below in combination with examples. Those skilled in the art will understand that the following embodiments are only used to illustrate the present disclosure and should not be regarded as limiting the scope of the present disclosure. Where specific techniques or conditions are not indicated in the embodiments, the procedures shall be carried out in accordance with the techniques or conditions described in the literature (for example, "Molecular Cloning Experiment Guide" by J. Sambrook et al., translated by Huang Peitang et al., third edition, Science Press) in the field or in accordance with the product specification. The reagents or instruments used without the manufacturer's indication are all conventional products that can be purchased commercially, for example, purchased from Sigma.

Embodiment 1

A method for expressing the anti-hTK1 single chain antibody of the embodiment of the present disclosure is as follows:

1. Material and Method
1.1. Material
   pET22b plasmid donated from the School of Basic Medical Sciences, Capital Medical University;
   Strain BL21(DE3) purchased from Huayueyang Biotechnology Co., Ltd.;
   Medium (peptone, yeast extract, glucose, purchased from Shanghai Aladdin Biochemical Technology Co., Ltd., potassium chloride, magnesium chloride, sodium chloride, purchased from Sinopharm);
   Agarose, 4Sgreen nucleic acid stain, IPTG, and ampicillin purchased from Shanghai Shenggong Biological Co., Ltd.;
   DNA gel recovery kit purchased from Qiagen Biotechnology Company;
   Glycine purchased from Sigma;
   Antibody gene synthesized by GenScript Biotechnology Co., Ltd.;
   Ncol and NotI restriction enzymes purchased from NEB Biotech;
   PCR kit purchased from Takara Biotechnology Company;
   T4 ligase purchased from Takara Biotechnology Company;
   Biotinylated anti-hTK1-IgY antibody (homemade);
   One-component TMB color developing solution purchased from Huzhou Yingchuang Biological Technology Co., Ltd.;
   Mltrafiltration centrifuge tubes purchased from Sartorius.
1.2 Instrument
   Bio-rad electrophoresis instrument, Bio-Rad Gel-XR+, Gel imaging system constant temperature shaking incubator (Shanghai Zhicheng), horizontal electrophoresis tank (Beijing Liuyi), T100 electrophoresis tank (purchased from Bio-Rad), MicroPulser electroporator (purchased from Bio-Rad), H2050R high-speed refrigerated centrifuge (purchased from Xiangyi), MMLTCSKAN Fc type microplate reader (purchased from Thermo).
1.3 Reagent
   SOC medium: 2% (W/V) Tryptone, 0.5% (W/V) Yeast Extract, 0.05% (W/V) NaCl, 2.5 mMKCl, 10 mMMgCl2, 20 mM glucose;
   SOB medium: 2% (W/V) Tryptone, 0.5% (W/V) Yeast Extract, 0.05% (W/V) NaCl, 2.5 mMKCl, 10 mMMgCl2, 1.5% agar powder, 100 µg/ml ampicillin;
   LB medium: Tryptone 10 g/L, Yeast extract 5 g/L, NaCl 10 g/L, containing 100 µg/ml ampicillin;
   TAE buffer(50*): Weigh 242 g Tris and 18.612 g EDTA in a 1 L beaker, add about 800 ml deionized water to the beaker and stir well, add 57.1 ml of glacial acetic acid, fully dissolve it, adjust the pH to 8.3 with NaOH, add deionized water to make the volume to 1 L, and store at room temperature;
   TE buffer(1*): 10 mMTris-HC11 mM EDTA PH=8.0;
   Protein extract: 36% sucrose, 20 mM pH7.4PBS buffer 2.5 mM EDTA;
   PBS buffer: Weigh 2.758 g $Na_2HPO_4 \cdot 2H_2O$, 0.232 g $NaH_2PO_4 \cdot H_2O$, 8.5 g NaCl, dissolve the volume to 1 L, and adjust the pH to 7.4;
   Glycine eluent: Weigh 7.5 g glycine and 8.775 g NaCl to dissolve and dilute to 1 L, and adjust the pH to 2.5 with 1M NaOH;
   PBST: Add Tween-20 to PBS buffer at 0.1%, then filter;
   Sulfuric acid stop solution: accurately measure 56 ml of sulfuric acid and carefully dissolve it in 944 ml of deionized water.

2. Method
2.1 Double Enzyme Digestion of the Target Fragment and pET22b Plasmid Vector Take the target single-chain antibody gene (the gene shown in SEQ ID NO: 2) and the vector pET 1 µg respectively, and add them to a 50 µl PCR tube, add 5 µl of NEB Buffer3.1 solution and 1 µl of Ncol and NotI restriction enzymes, dilute to 50 µl, react at 37° C. for 1 h, and recover the product by agarose gel electrophoresis.

2.2 Enzyme Chain Reaction

Mix the recovered double enzyme digestion product into the PCR tube according to the target gene fragment: plasmid vector=3:1 molar amount, add 2*buffer and 1 µl T4 ligase according to the Takara T4 ligase instructions, ligate overnight at 16° C., and purify the product by ethanol/sodium acetate precipitation.

2.3 Preparation of Electrocompetent Cells

Inoculate BL21(DE3) into 5 ml LB medium, culture overnight at 37° C. with shaking, then remove, inoculate into 500 ml LB medium at 1:100, cultivate at 37° C. to OD=0.5, centrifuge at 5000 r/min for 10 min, remove the medium, then add ⅕ of the volume of the bacteria liquid to suspend the cells in pre-cooled sterile deionized water, centrifuge at 5000 r/min for 20 min, discard the supernatant, add 10% pre-chilled sterilized glycerin of 1/10 of the volume of the bacterial solution, centrifuge at 5000 r/min for 20 min, discard the supernatant, then rinse with 1/50 volume of pre-cooled sterilized 10% glycerol, centrifuge at 5000 r/min for 20 min, discard the supernatant, and suspend the cells in 2 ml of 10% glycerol and suspend the cells in 50 µl/tube.

2.4 Electric Conversion

40 µl BL21(DE3) electrocompetent cells, melt on ice, add 1 µl enzyme to recover the product, place on ice and mix for 2 min, add 1 mm electric shock cup, 1.8 Kv electric shock for 5 ms, immediately add 1 ml SOC medium, shake culture at 37° C. for 1 h, take out the bacterial solution and evenly spread it on the SOB solid medium containing 100 µg/ml ampicillin, and incubate overnight at 37° C.

2.5 Induced Expression

Pick a single colony, culture it at 37° C. for 4 h, add 1:100 to LB medium containing ampicillin, culture it at 37° C. to OD600=0.6, add IPTG to a final concentration of 0.5 mm, and induce overnight at 25° C.

2.6 Expression Extraction

Centrifuge at 5000 r/min for 10 min to collect the bacteria, add the same amount of protein extract, mix the suspended cells thoroughly at room temperature, about 10 min, then quickly add 5 times the volume of pre-cooled sterile deionized water, equilibrate for 20 minutes, centrifuge at 8000 r/min at 4° C. for 15 minutes, the supernatant being the target single-chain antibody extract, and add PMSF protein protectant.

2.7 Affinity Chromatography

Equilibrate the column with 0.01M tris base for three times, add the single-chain antibody extract obtained in "Step 2.6" filtered through a 0.45 µm filter membrane to be purified, place it on a shaker for 2 to 4 hours at room temperature, wash the column with 0.01M tris base for more than three times to remove unbound impurities, elute the antibody bound to the column with 9 ml 0.1M pH 2.5 glycine, add 1 ml 1M pH8.0 Tris-HCl solution to the EP tube to neutralize the eluted antibody, dialysis in 0.01M PBS 4 times with an interval of 8 hours to change the fluid once, put the antibody solution into an ultrafiltration centrifuge tube with a pore size of 10 kDa and concentrate to about 2 ml to obtain purified anti-hTK1 monoclonal antibody.

2.8 ELISA Comparative Test

Prepare the purified and measured concentration of the monoclonal antibody and the biotinylated the anti-hTK1-IgY antibody to the same 0.1 μg/ml with PBS, and dilute 6, 36, 216, 2196, 7776, 46656 times respectively, the specific concentration is shown in the table below, add 1 μg/ml TK1 antigen-coated microwell reaction plate to 100 μl/well and react for 1 h at 37° C., wash with PBST 3 times, then add 1:10000 diluted SA-HRP and react at 37° C. for 1 hour, wash with PBST 3 times, add one-component TMB color developing solution, react at 37° C. for 10 minutes, terminate the reaction by adding sulfuric acid stop solution, and read the OD450 with the microplate reader.

|  |  | 0.1 μg/ml anti-hTK1 scfv | 0.1 μg/ml biotinylated anti-hTK1-IgY antibody |
|---|---|---|---|
| Dilution factor | 6 | 2.1034 | 3.2414 |
|  | 36 | 0.8177 | 0.6073 |
|  | 216 | 0.3704 | 0.2469 |
|  | 1296 | 0.2374 | 0.1896 |
|  | 7776 | 0.1934 | 0.1734 |
|  | 46656 | 0.1799 | 0.1861 |

3. Results

Figure 1:
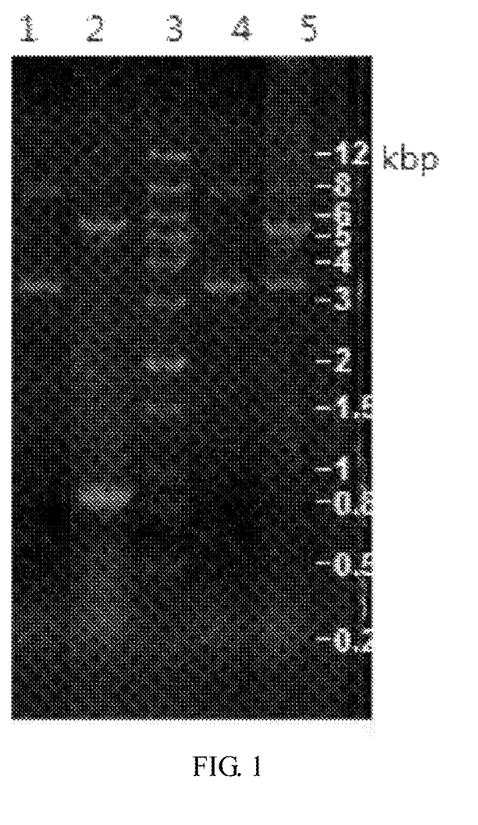
FIG. 1 shows a schematic diagram of double digestion electrophoresis result according to an embodiment of the present disclosure.
Figure 2:
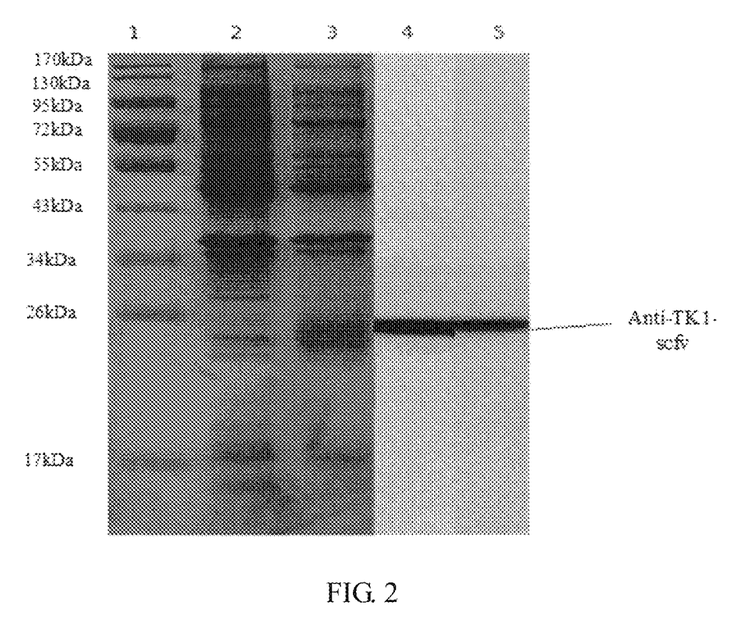
FIG. 2 shows a schematic diagram of SDS-PAGE electrophoresis result according to an embodiment of the present disclosure.
Figure 3:
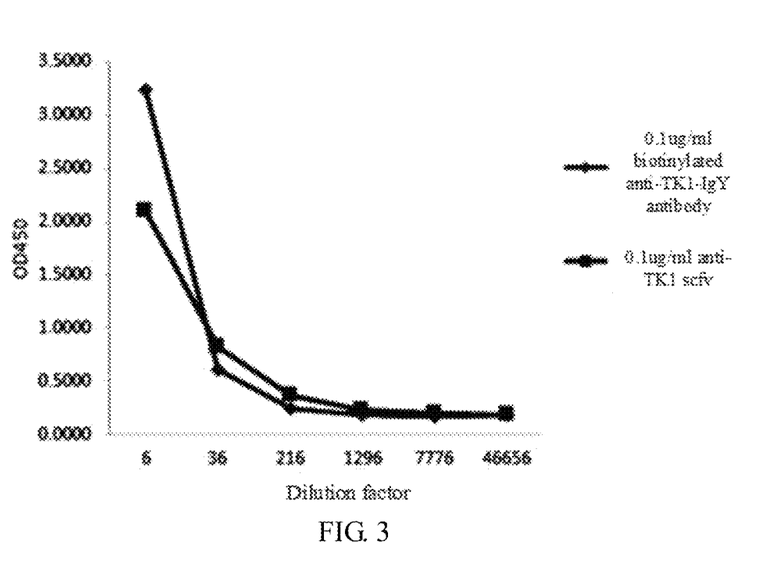
FIG. 3 shows a schematic diagram of ELISA test result according to an embodiment of the present disclosure.

The experimental results are shown in FIG. 1 to FIG. 3.

3.1 Double Enzyme Digestion Electrophoresis Result

FIG. 1 shows the result of agarose gel electrophoresis of the recombinant single-chain antibody expression plasmid and the original empty Pet22b+ plasmid Not I and Nco I restriction endonucleases. Lane 1 is a recombinant scfv-pET22b+ plasmid. Lane2 is a recombinant scfv-pET22b+ plasmid Not I and Nco I digested product. Lane 3 is DNA Lader. Lane 4 is a pET22b+ empty plasmid. Lane 5 is a product of pET22b+ empty plasmid Not I and Nco I digested, indicating that the recombinant plasmid contains the target gene.

SDS-PAGE Electrophoresis Result

The result of SDS-PAGE electrophoresis is shown in FIG. 2. Lane 1 is a protein Marker. Lane 2 is an uninduced control of recombinant single-chain antibody expressing bacteria. Lane 3 is a broken liquid of recombinant single-chain antibody expressing bacteria after induction. Lane 4 is 100 mm eluent of Ni-NTA affinity chromatography column. Lane 5 is 200 mm eluent of Ni-NTA affinity chromatography column, indicating that the purified protein is a single-chain antibody.

3.3 ELISA Test Comparison Result

The ELISA test result is shown in FIG. 3. The single-chain antibody is closer to the biotinylated anti-hTK1 antibody in terms of antibody titer, but its ability to withstand dilution is better.

In the description of this Specification, description with reference to the terms "an embodiment", "some embodiments", "examples", "specific examples", or "some examples" etc. mean that the specific features, structures, materials or characteristics described in combination with the embodiment or example are included in at least one embodiment or example of the present disclosure. In this Specification, the schematic representations of the above terms do not necessarily refer to the same embodiment or example. Moreover, the described specific features, structures, materials or characteristics may be combined in any one or more embodiments or examples in a suitable manner.

Although the embodiments of the present disclosure have been shown and described, those of ordinary skill in the art can understand various changes, modifications, substitutions and modifications can be made to these embodiments without departing from the principle and purpose of the present disclosure. The scope of the present disclosure is defined by the claims and their equivalents.

What is claimed is:

1. A recombinant chicken IgY scFv antibody raised against human thymidine kinase 1 and expressed in prokaryotic cells, comprising the amino acid sequence shown in SEQ ID NO: 1.

2. A recombinant chicken IgY monoclonal antibody raised against human thymidine kinase 1 and expressed in prokaryotic cells, comprising the amino acid sequence shown in SEQ ID NO: 1.

3. An isolated nucleic acid, wherein the isolated nucleic acid encodes the scFv antibody of claim 1.

4. The isolated nucleic acid of claim 3, wherein the isolated nucleic acid includes the nucleotide sequence shown in SEQ ID NO: 2.

5. An isolated nucleic acid, wherein the isolated nucleic acid encodes the monoclonal antibody of claim 2.

6. The isolated nucleic acid of claim 5, wherein the isolated nucleic acid includes the nucleotide sequence shown in SEQ ID NO: 2.

7. A vector for prokaryotic expression, comprising the isolated nucleic acid of claim 3.

8. The vector of claim 7, wherein the vector is an expression vector and is for transformation in prokaryotic cells.

9. A method for preparing the scFv antibody of claim 1, comprising:
culturing host cells containing a nucleic acid encoding the amino acid sequence shown in SEQ ID NO: 1, under conditions suitable for protein expression and secretion, to obtain the scFv antibody.

10. A method for preparing the monoclonal antibody of claim 2, comprising:
culturing host cells containing a nucleic acid encoding a monoclonal antibody comprising the amino acid sequence shown in SEQ ID NO: 1, under conditions suitable for protein expression and secretion, to obtain the monoclonal antibody.

11. An immunoconjugate, comprising:
the scFv antibody of claim 1; and
a conjugate moiety selected from a group consisting of drugs, toxins, cytokines, radionuclides or enzymes.

12. An immunoconjugate, comprising:
the monoclonal antibody of claim 2; and
a conjugate moiety selected from a group consisting of drugs, toxins, cytokines, radionuclides or enzymes.

* * * * *